(12) United States Patent
Pawluczyk et al.

(10) Patent No.: US 7,854,705 B2
(45) Date of Patent: Dec. 21, 2010

(54) EX VIVO VERIFICATION OF BIOPSY TISSUE SAMPLES

(76) Inventors: Olga Pawluczyk, 280 Golf Course Road, Conestogo, Ontario (CA) N0B 1N0; Cameron Piron, 339 Glenridge Dr., Waterloo, Ontario (CA) N2J 3W7

( * ) Notice: Subject to any disclaimer, the term of this patent is extended or adjusted under 35 U.S.C. 154(b) by 1201 days.

(21) Appl. No.: 11/014,675

(22) Filed: Dec. 16, 2004

(65) Prior Publication Data

US 2006/0173266 A1 Aug. 3, 2006

(51) Int. Cl.
 *A61B 5/05* (2006.01)
 *A61B 5/055* (2006.01)
(52) U.S. Cl. .................................... 600/562; 600/420
(58) Field of Classification Search .................. None
See application file for complete search history.

(56) References Cited

U.S. PATENT DOCUMENTS

| | | | |
|---|---|---|---|
| 4,572,203 A | 2/1986 | Feinstein | 424/9.52 |
| 4,930,516 A | 6/1990 | Alfano et al. | 600/477 |
| 5,093,106 A | 3/1992 | Dzbanovsky et al. | 424/9.6 |
| 5,419,323 A | 5/1995 | Kittrell et al. | 600/476 |
| 5,869,023 A * | 2/1999 | Ericcson et al. | 424/9.36 |
| 6,066,102 A | 5/2000 | Townsend et al. | 600/564 |
| 6,091,985 A | 7/2000 | Alfano et al. | 600/476 |
| 6,174,291 B1 | 1/2001 | McMahon et al. | 600/564 |
| 6,421,553 B1 | 7/2002 | Costa et al. | 600/476 |
| 6,521,209 B1 | 2/2003 | Meade et al. | 424/9.3 |
| 6,526,299 B2 | 2/2003 | Pickard | 600/310 |
| 6,593,101 B2 | 7/2003 | Richards-Kortum et al. | 435/29 |
| 6,697,652 B2 | 2/2004 | Georgakoudi et al. | 600/310 |
| 6,723,303 B1 | 4/2004 | Quay | 424/9.52 |
| 2002/0164810 A1 | 11/2002 | Dukor et al. | 436/64 |
| 2003/0191397 A1 | 10/2003 | Webb et al | 600/476 |
| 2003/0199754 A1 | 10/2003 | Hibner et al. | 600/411 |
| 2004/0254445 A1 | 12/2004 | Bittner | 600/410 |

FOREIGN PATENT DOCUMENTS

| | | |
|---|---|---|
| WO | WO00/68665 | 11/2000 |
| WO | WO 01/28412 | 4/2001 |
| WO | WO 2004/048988 | 6/2004 |

OTHER PUBLICATIONS

Bugaj et al. Novel Fluorescent Contrast Agents for Optical Imaging of In Vivo Tumors Based on a Receptor-Targeted Dye-Peptide Conjugate Platform; Journal of Biomedical Optics, vol. 6, No. 2 (2001) pp. 122-133.*

Young et al. Confidence Images for MR Spectrscopic Imaging; Magnetic Resonance in Medicine, vol. 44 (2000) pp. 537-545.*

M. Kriege, C.T.M. Brekelmans, C. Boetes, J. Klijn, at al. "Efficacy of MRI and Mammography for Breast-Cancer Screening in Women with a Familial or Genetic Predisposition." N Engl J Med 2004; 351:427-437.

Gregory Palmer, et al. "Optimal Methods for Fluorescence and Diffuse Reflectance Measurements of Tissue Biopsy Samples" Lasers in Surgery and Medicine. 30:191-200 (2002).

Nicole Kline et al. "Raman Chemical Imaging of Breast Tissue" Journal of Raman Spectroscopy, vol. 28. 119-124 (1997).

Ramasamy Manoharan et al. "Histochemical Analysis of biological tissues using Raman Spectroscopy", Spectrochimica Acta Part A..52 (1996) 215-249.

K. E. Shafer-Peltier, et al. "Raman microspectroscopic model of human breast tissue: implications for breast cancer diagnosis in vivo". Journal of Raman Spectroscopy, 2002, 33:552-563.

Ntziachrstos V, et al. "Concurrent MRI and diffuse optical tomography of breast after indocyanine green enhancement" PNAS, Mar. 14, 2000, vol. 97, No. 6, 2767-2772.

* cited by examiner

*Primary Examiner*—Rebecca E. Prouty
*Assistant Examiner*—Paul C. Martin
(74) *Attorney, Agent, or Firm*—Mark A Litman & Associates, PA

(57) ABSTRACT

An instrument for verification of presence of image enhancing, contrasting agent in a biopsy sample which was obtained by imaging the lesion area with an imaging modality which is sensitive to the contrasting agent. In one embodiment of the invention, an optical spectrometer is used to analyze biopsy samples for the presence of gadolinium enhanced Magnetic Resonance Imaging contrasting agent which typically pools in breast tumors.

19 Claims, 6 Drawing Sheets

EX VIVO VERIFICATION OF BIOPSY TISSUE SAMPLES

BACKGROUND OF THE INVENTION

1. Field of the Invention

The present invention relates to biopsy tissue verification and more specifically to devices and methods which inspect excised tissue for the presence of endogenous or exogenous contrasting agents used to better image clinically interesting regions of the body, preferably by non-destructive observation or testing of excised tissue.

2. Background of the Art

The field of detection and diagnosis of cancerous tumors, pre-malignant, malignant and other lesions and disorders is very broad and has been the subject of much research. Typically, an imaging modality including, but not limited to X-ray imaging, tomography, MRI, ultrasound, PET, nuclear imaging, palpation and visual inspection is first used to locate an area of clinical significance within the patient. Many of these techniques use the inherent biophysical contrast unique to the pathology to visualize, or diagnose the pathology. These endogenous techniques are beneficial as external contrast agents are not required and therefore directly measure pathology of interest. Once the presence of a lesion is detected with some imaging method, a biopsy is performed to extract the suspicious tissue from the patient and test it for presence of abnormal pathology. This can be done either in an open procedure or in a percutaneous, less invasive, procedure. One limitation of these methods is that optimally an excised sample should be checked whether it contains the lesion structure, before the patient can be released. This is a time consuming procedure, requires transfer of the biopsy sample from the procedure room, and does not easily fit into standard biopsy procedures. In most cases this can not be accommodated, and therefore there remains a degree of uncertainty as to whether the excised tissue does in fact include part or all of the tissue identified by the original imaging technique.

Increasingly, external exogenous contrast media are introduced into the patient in order to enhance the ability to visualize the pathology during in vivo testing/examination procedures such as MRI, X-ray, fluoroscopy and the like. Before or during a typical biopsy procedure, a contrasting agent is introduced into the bloodstream of the patient (either intravenous or intra-arterial, injection, orally or some other appropriate delivery method), with the expectation that the contrasting agent enters the lesions of interest and by the non-invasive observation of the contrast created by differential absorption into the lesion, the lesion can be more readily observed. Most imaging modalities have contrasting agents specifically designed to a) collect mainly in pathologically significant lesions and b) to create recognizable by selected modality signal different than in areas with little or no contrasting agent.

The contrast agents can stay within the tumor for different amounts of time, so that the agent either dissipates quickly or can accumulate in the areas of interest for long periods of time. The longer persistence of contrast agents can assist in long procedures such as surgical biopsy.

The contrast agents may also be used in different combinations. Combining two or more agents which are used for different imaging modalities helps in co-registration of images, better imaging and improved diagnostics. It is possible to add a component to an existing contrast agent, or modify an existing contrast agent, to make it better detectable by other methods, for example optical spectroscopy.

Contrast agents currently include and are not limited to paramagnetic molecules such as ones using chelated gadolinium. These allow for better control of relaxation times in MR imaging ["Breast Lesions: Correlation of Contrast Medium Enhancement Patterns on MR Images with Histopathological Findings and Tumor Angiogenesis." Radiology 1996], thus providing better contrast of structures with high contrast agent concentration. For X-ray based imaging, highly x-ray absorbing compounds such as iodine, Barium, or Barium Sulfate are used. Ultrasound contrasting agents are generally formed from microbubbles, which resonate under ultrasound frequencies. Optical applications such as optical coherence tomography (OCT) use bubbles filled with light-scattering media [J. K. Barton, J. B. Hoying, and C. J. Sullivan, "Use of microbubbles as an optical coherence tomography contrast agent," Acad. Radiol. 9, S52-5 (2002)] or fluorescing markers attaching to particular cellular features. In ultrasound, the use of microbubble contrast agents has been demonstrated in the visualization of lesions in the kidney, liver and breast. Thus far, ultrasound contrasting agents have penetrated the medical imaging field to a much lesser degree than those used for MRI.

The application of the contrast agent field is now expanding to include ultrasound as presented by Feinstein (U.S. Pat. No. 4,572,203) and Quay (U.S. Pat. No. 6,723,303) and multimodality contrast agents as presented by Meade et al. (U.S. Pat. No. 6,521,209) for optical and MRI combined contrast agent. Multi-modality contrast agents have been proposed which can be used in improved visualization in more than one modality. The clinical application of these agents has not yet been realized. These agents include:

- microbubbles+gadolinium combined
- gadolinium+flourophores
- gadolinium+optical dye
- gadolinium+antibody markers+flourophores Contrast agents combined with antibodies have been developed to enable visualization of a specific antigen. Instead of focusing on gross pathology, actual chemical changes within cells can be targeted with these contrast agents. This aids in detection and imaging of specific biochemical processes in patient's or laboratory specimens. Efforts are currently underway to combine this concept with the multitude of contrast agents available.

In abovementioned radiological imaging techniques, there still exists a requirement of obtaining a tissue sample through biopsy to determine clinical management. This is always a difficult procedure, and it is prone to error. Problems with biopsy include at least:

- inability to access all regions of tissue appropriately
- inability to visualize the needle entering the lesion properly
- disruption of the tissue after large needle gauge samples (vacuum-assisted)
- difficulties with confirmation that the sample actually being taken from the appropriate location determined with an imaging modality Optical techniques have been proposed to help in the guidance of biopsy needles to targets based on endogenous signal from pathological tissues in specific applications. An overwhelming majority of research is focused on attempts to better position the needle into tissue of interest, for example by Hibner et al. (U.S. Pat. No. 0,199,754A1), demonstrates how a supplementary device such as spectroscopic fibre, can be used in conjunction with a biopsy gun to better analyze the biopsy site. However, there is little done to validate whether the actual excised tissue matches the region viewed with the imaging method guiding the biopsy. Furthermore, no attempt has been made in this patent to measure or detect the specific signature of an exogenous contrast agent.

Most imaging and sampling techniques are focused on the actual diagnosis of pathology in vivo in order to avoid or supplement the acquisition of a tissue sample. Many of these techniques perform well ex vivo, however once applied in vivo, in a much more challenging clinical environment, the techniques breakdown and lose their clinical utility. Some techniques have been also developed to examine excised tissue for pathology. These include taking a radiograph and checking for pathology induced radiographic changes such as calcifications or structural changes. Excised biopsy samples are typically examined by pathologists who inspect microscopic slides for structural changes to cells due to disease processes. The results from the examination of a sample by a pathologist determine the final diagnosis of the targeted tissue. As there may be uncertainty to whether the correct volume of tissue has been sampled, the results from the pathologist may also reflect this uncertainty.

It is in very rare circumstances that a pathologist will be able to examine the results of a biopsy sample, or surgical excision before the patient is released from the radiologist or surgeon. Therefore, the decision whether to obtain more tissue samples, or remove a larger section of tissue can not be guided by a close examination of the tissue during a typical procedure. Instead, biopsy verification is typically performed after a patient has been released. When the biopsy excision is deemed unsatisfactory, the patient is recalled to perform another procedure.

Currently, during a typical breast biopsy performed under any of the available imaging modalities, the radiologist may examine the biopsy samples visually to determine whether the samples appear to have arisen from glandular tissue, which is more likely to present abnormal pathology, or from fatty tissue which normally does not contain malignancies. This procedure may be augmented by looking at whether the samples float, or sink in the saline solution, indicating the relative density of the sample.

In a standard X-ray examination, biopsy samples obtained from lesions, which demonstrated micro-calcifications are X-rayed to validate that these micro-calcifications are present in the sample. This verifies that the samples correlate to what was evident on the mammography images. This is often done while the patient is still immobilized in the stereotactic biopsy device so the results of the tissue sample X-ray can guide the radiologist to obtain more samples from the region of interest. Performing this verification after the patient has been removed from the apparatus is not as beneficial as it cannot guide clinical management decisions at that time; however, it may impact the degree of confidence to which the radiologist may accept a pathological diagnosis that does not match the imaging presentation. The radiographic practice is extended to the surgical suite, where lesions that are surgically excised are processed in a specimen radiograph. This device is a small X-ray machine that produces an X-ray image of the excised tissue in a non-destructive manner. The image is obtained with the anticipation that there will be some X-ray imaging indication of the tumor within this sample (region of dense tissue, micro-calcification, indication of structure) from which the surgeon can verify that the correct region was removed and that proper margins were obtained around the lesion. This practice can often be helpful; however, many lesions are not well visualized using X-ray and do not present an X-ray evident presentation [M. Kriege, C. T. M. Brekelmans, C. Boetes, J. Klijn, et al. Efficacy of MRI and Mammography for Breast-Cancer Screening in Women with a Familial or Genetic Predisposition. N Engl J Med 2004; 351: 427-437].

This is becoming more problematic as modalities other than X-ray are increasingly being used to detect lesions and guide interventions (i.e., MRI, US [ultrasound], CT [computed tomography]). There is no simple way of verifying whether the biopsy sample obtained matches with the area of interest on an image used to guide the biopsy.

Techniques such as mass spectroscopy, laser induced breakdown spectroscopy, chemical assays and others are based on the destruction of the tissue. Although these methods are very accurate and sensitive to the measurement of trace amounts of chemical compounds and could be used to determine the presence of contrast agent within the sample, they are not appropriate in a clinical setting where further histopathological analysis is required for normal patient management.

Generally, compounds used as contrast agents have molecular structure alien to molecules of human tissue, or are presented in concentrations greatly differing from those normally found in the body. Therefore, the inventors suggest that the contrast agents should be detectable by methods sensitive to the molecular composition of the sample or based on large variations in concentrations of a specific chemical compound. For this purpose, application of non-destructive optical spectroscopic methods is proposed. Of course, alternative imaging technologies can be used for observation and identification of the contrast agents. Any non-destructive observation technique may be used, preferably non-destructive observation, detection and/or measurement techniques of electromagnetic radiation.

As with all other molecules, the molecules of substances used as the contrast agent should demonstrate specific spectral changes in the spectrum of the interacting radiation, when illuminated with radiation in the UV, visible and/or infrared spectra, due to the energy shift in molecular bonds when photons of electromagnetic radiation interact with a molecule. Using spectrum analysis methods those changes can be recognized, identified and used for determination of the concentration of a specific compound within a sample.

Optical techniques in medicine have been used for centuries, starting with visual inspection of skin lesions, and diagnosis based on their coloring. Currently, spectroscopic methods are used to measure the spectral dependence of absorption, transmittance, reflection, ordinary and Raman scattering of electromagnetic radiation, as well as the spectral composition of radiation produced as a result of fluorescence. The data obtained in such a way can be used for the determination of presence and concentration of specific compounds in the measured sample.

Interaction of electromagnetic radiation with tissue is already used to obtain useful information about biological systems. The typical medical applications of electromagnetic radiation in the 400-1500 nm region are optical tomography and optical biopsy for imaging; photodynamic therapy and photo-induces thermotherapy for intervention. Autofluorescence and fluorescence of injected fluorescing or phosphorescing contrast agents has also been used to provide a better contrast of suspicious lesions as compared to normal tissues both in vivo and ex vivo as shown by Alfano et al. (U.S. Pat. No. 4,930,516 and U.S. Pat. No. 6,091,985).

U.S. Pat. No. 6,214,550 (Malins) describes methods of screening for a tumor or tumor progression to the metastatic state. The screening methods are based on the characterization of DNA by principal components analysis of spectral data yielded by Fourier transform-infrared spectroscopy of DNA samples. The methods are applicable to a wide variety of DNA samples and cancer types. A model developed using multivariate normal distribution equations and discriminant analysis is particularly well suited for distinguishing primary cancerous tissue from metastatic cancerous tissue.

Photodynamic therapy requires the delivery of optically active agent into a targeted area of the body, and then using very specific light source (most often single-wavelength laser) to activate the agent and thus destroy the tissues in which the agent has collected. Many patents exist for the design of photosensitizing agents that can collect in different types of tissues and that can be activated with different types of light sources. The specificity of the agents as well as need for agents that have no adverse effects still is driving research into this method of cancer treatment.

Optical biopsy generally involves delivery of light to a tissue sample with an optical fiber or an optical relay. The light interacts with the tissue (with minimum or no destruction of tissue), and returning light is collected by an endoscope or biopsy forceps for spectroscopic analysis such as fluorescence spectroscopy as shown by Webb (U.S. Pat Appl No. 2003/10191397A1) autofluorescence shown by McMahon et al. (U.S. Pat. No. 6,174,291) or by Raman spectroscopy and others. This method is generally used in a non-invasive procedure using an endoscope or a contact probe, but has also been used for invasive procedures where the probe is placed within a biopsy needle as mentioned by Townsend et al. (U.S. Pat. No. 6,066,102). To classify tissues, either their intrinsic optical properties are used, or specifically designed optical markers, which are absorbed by the target tissue, are injected into the bloodstream and detected when they interact with light.

Previous light-based imaging applications depend either on easily detectable differences of optical properties of lesions and normal tissues or on detection of optical markers usually not recognizable by non-optical methods, but producing easily recognizable optical signal and whose concentration increases in lesions. The main concept of the present invention is to use the difference in spectral properties of tissue molecules and molecules of substances used as contrast agents for non-optical imaging methods. It is well known from physics and molecular spectroscopy that during the interaction of electromagnetic radiation with tissues, photons of different energy interact in different ways with different molecules. The photons are either absorbed, scattered or have their energy level changed by energy transfer to or from the compound molecules present. Spectroscopy allows for the quantitative analysis of such interactions and can allow the identification of compounds and structures being analyzed. There exist several spectroscopic methods, which can be used for this purpose.

Absorbance spectroscopy in the UV-visible-IR region is based on the absorption of incoming photons by the sample. Specific molecular bonds absorb incoming photons and are thus propelled into higher energetic states. When a sample is illuminated by radiation from a source producing radiation in a wide spectral range, the multiple molecules within the sample interact differently with photons of different wavelengths, causing the sample specific changes in the spectrum of the interacting radiation. By detecting these changes, it is possible to determine the presence and the concentration of a specific compound within the sample. Majority of organic and non-organic molecules produce strong basic absorption bands in mid-range and far infrared spectral ranges with much weaker overtones and combination absorption bands in near infrared and visible ranges. In case of biological samples, these signals overlap with the very strong and wide absorption bands produced by the water present in every biological tissue. The spectral overlap of signal obtained from the contrasting agent present for a specific modality and the endogenous signal of the biological sample, including its water signal, creates significant difficulties in the detection of the alien molecules of the contrasting agent; however, it is possible to overcome these problems by using high performance spectroscopy methods such as absorption spectroscopy, MR spectroscopy or other spectroscopic methods such as scattered light spectroscopy, Raman spectroscopy and other similar methods.

The difficulty in the spectroscopic determination of the presence of a compound arises when multiple compounds are present within a sample or when some compounds such as water have predominant contribution to the measured spectrum. However, the majority of substances used as contrast agents for imaging modalities have structures substantially different from those contained organic matter; therefore, they produce signals different from those produced by components of organic substances. In these cases, it is important to recognize how to extract the small spectral contribution of a contrast agent from a spectrum containing strong signal from the predominant water absorption. This can be achieved by using high performance spectroscopic methods supported by advanced data analysis techniques including but not limited to partial least square regression with numerous modifications, principal component analysis, neural networks, wavelet transforms, clustering, genetic algorithms, and similar methods alone or in combination, possibly enhanced by other techniques which enable the extraction of information distributed across a wide spectral range.

Most of the abovementioned techniques are already used in diagnosis and treatment of disease processes. Understanding of spectral characteristics of tissue allows for the determination of the structure and chemical composition of the sample. However, an area of the field of medicine that remains unexplored is the use of advanced spectrographic techniques to validate whether tissue removed from a patient in a clinical setting contains tissue of clinical interest that was seen with a given imaging modality when a contrasting agent was used. The constraints on this problem are substantially different than in vivo diagnosis, and present a clear and significant clinical benefit by enhancing the physician's ability to make more informed decisions. Furthermore, such a method may provide clear benefits in that it is a non-destructive examination of the excised sample. After a spectroscopic verification, the unchanged sample can be reintroduced back into the processing in a typical biopsy procedure.

Consequently, a method which quickly validates whether a specific biopsy sample contains an elevated concentration of an imaging contrast agent and thus comes from a region of interest as seen on a biopsy guiding image, should be very beneficial. The measured concentration of contrast agent in said biopsy sample may or should correlate with the intensity, or contrast variation observed in same region of interest in the related imaging modality in a manner that is well understood in the field of medical imaging physics. Such a method can provide better clinical guidance, provide better confidence in actual pathological diagnosis of the sample, will save unnecessary time where the patient has to wait for biopsy confirmation, and will reduce patient recalls and misdiagnosis based on examination of an improper biopsy sample. Furthermore, extension of this concept to aid in the surgical excision of pathology, with or without the use of contrast agents which are less prone to contrast-agent temporal uptake variation or introduced at the time of surgery, may lead to more accurate tumor resection.

SUMMARY OF THE INVENTION

Biopsies or surgical samples are examined for the presence of a contrasting agent (exogenous material with or without the presence of endogenous material) to identify an area of clinical interest. The proposed method and apparatus contemplates that contrast agents usually have molecular structure different from those normally seen within the body, hence an interaction with electromagnetic radiation indicative of these 'different' structures should demonstrate a specific spectral signature different from the signature(s) produced by the normal components of the tested biological tissues. These changes in the signature of the signal can be recognized by an imaging or observation system, a spectrum analyzer or a spectrometer that examines biopsy sample composition by the quantification of the spectral changes produced as a result of the interaction between electromagnetic radiation and the sample exposed to it.

Based on the concentration of the contrast agent within the obtained sample, information relating to the likelihood that the particular sample was within the region of interest on the guiding image can be provided from non-destructive, or minimally destructive testing of the sample to observe the presence of the contrasting agent in relative concentrations indicative of abnormal tissue. This will in turn increase confidence that the biopsy sample obtained is actually that from the region of concern. Due to the potential for non-destructive activity in the proposed verification, an improvement in the biopsy accuracy and speed is possible without greatly influencing the established procedures now in place.

BRIEF DESCRIPTION OF THE FIGURES

For a better understanding of the presently described technology, and to show more clearly how the technology may be carried into effect, reference will now be made, by way of non-limiting examples, to the accompanying drawings, in which.

DETAILED DESCRIPTION OF THE INVENTION

Figure 1:
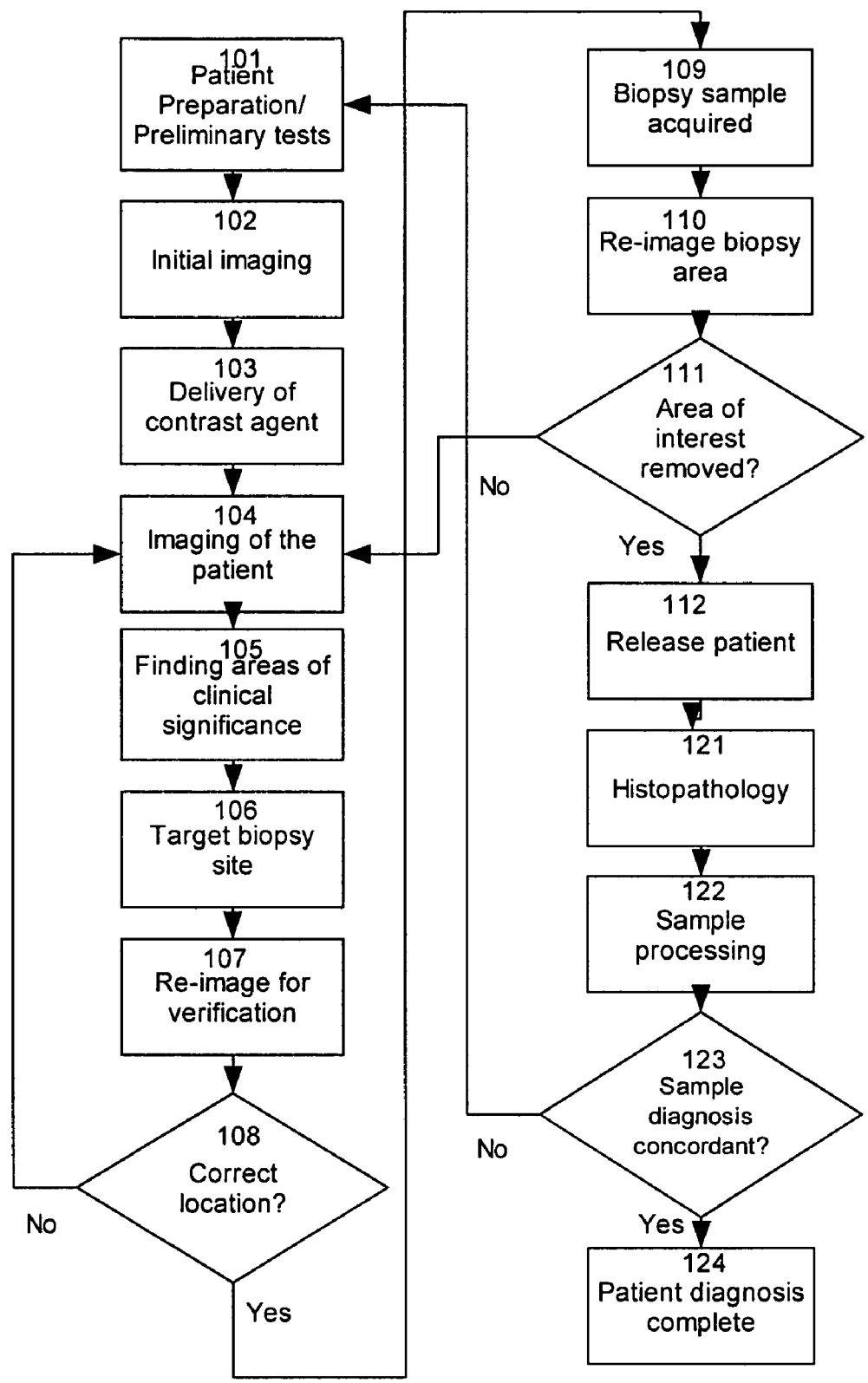
FIG. 1: Is a flowchart demonstrating the decision making process during a presently applied biopsy procedure.

A method indicates a likely presence of abnormal tissue within an ex vivo sample of tissue by providing observable agent to a region of interest of a patient; removing from the patient a tissue sample from the region of interest to provide a removed tissue sample; non-destructively or minimally destructively observing the removed tissue samples under conditions that allow observation or detection of the non-destructively observable agent; and evaluating results of the observation or detection of the observable agent within the removed tissue sample. Observation may be by destructive, partially non-destructive or non-destructive techniques, as described herein. The method may evaluate results by assessing a likelihood of the presence of abnormal tissue within a sample or evaluating results to determine whether the removed tissue sample has been taken from the region of interest. After removing the sample, and preferably before or after evaluating results, histopathic examination may be performed on the removed tissue sample, which may remain intact. The method may have the non-destructive or minimally destructive observation comprise spectroscopic analysis; at least one procedure selected from the group consisting of colorimetry, sonography, spectroscopy and magnetic resonance imaging of the removed tissue sample. The method may utilize intensity changes or density differences from the removed tissue sample to provide information that is evaluated. The method may use observable agents that are known to be absorbed differently by normal tissue and abnormal tissue. The method may have the non-destructive or minimally destructive observation comprise assessing concentration of the observable agent in the tissue by measuring or detection levels of absorption of electromagnetic radiation at least at one preselected wavelength or one or more spectral bands in at least one of the UV, visible and IR spectral ranges without the damage to the tested tissue. The preferably non-destructive observation may comprise any concentration measuring technique.

A system may be used for indicating a likely presence of abnormal tissue within an ex vivo sample of tissue comprising: an imaging system for observing a region of tissue within a patient; at least one observable agent that can be delivered to a region of interest of a patient;

a tissue removing device that may be used within the imaging system;

a system for non-destructively or minimally destructively observing removed tissue samples under conditions that allow observation or detection of the observable agent; and a data storage system or processor that receives data from the system for non-destructively or minimally destructively observing removed tissue.

The terms "spectrum analyzer" and "spectrometer" are used interchangeably in the description and in the claims.

The terms "tissue sample", "biopsy sample" and "surgical sample" are used interchangeably in the description and in the claims.

In one aspect, the presently described technology relating to an invention provides a method to verify whether an excised tissue sample has been collected from an area of clinical significance through the detection or measurement of the concentration or presence of exogenous contrast media with or without additional endogenous signal measurement which can be used to locate areas of interest and possible pathology in an organism which undergoes some form of imaging which benefits from the presence of the specific contrasting media. This methodology is done for the purpose of determination of the likelihood that the excised sample was actually contained within the region of interest as seen by the imaging modality.

In another aspect, the presently described technology relating to an invention provides means to measure the concentration or presence of contrast media using spectroscopic methods or high performance spectroscopic methods.

It is well known for these skilled in the art that imaging modalities such as x-ray imaging, magnetic resonance imaging (MRI), ultrasound, optical computer tomography (OCT), x-ray computer tomography (CT), positron emission tomography (PET) and others can provide images with better clinical information, if an exogenous contrast agent is injected into a patient, thereby providing better contrast between structures of interest and those with no medical significance. Typically, contrast agents tend to interact with clinically significant structures in such a way, that a greater concentration of the agent is present within the structure than outside in non-significant tissues. Therefore, the concentration distribution of the contrast agent provides the externally (non-obtrusive observation, such as radiography, sonogram, fluoroscopy, MRI, etc.) performed imaging modality with a better contrast differentiating the region of significance from other areas. In a typical imaging examination, if the applied imaging method does not show abnormal concentration of the contrast agent the patient either is deemed disease free, or if other suspicions exists, is directed for further testing with different modality possibly using a different contrast agent. In the case when the existence of a region with increased concentration of contrast agent is identified, there still exists a need for pathology tests of the structure to determine its medical diagnosis. These histopathology tests can be performed directly on extracted tissues in pathology laboratory; therefore a suitable sample has to be extracted from the identified structure. To reduce the suffering of the patient, such extraction is typically performed with a minimally invasive technique which is guided with an imaging modality. Unfortunately, it is often difficult to determine the precise position of the biopsy tool with respect to the clinically significant area, and in spite of the physicians' best effort there still exists some probability that the sample will be extracted from medically insignificant place, or the sampling tool or method does not extract the tissue in the expected manner. Therefore there exists a need to verify that the sample has been collected from the intended position as indicated on imagery. Presently, validation is typically performed only after histopathologic analysis of the extracted sample. The complete test consists of many steps, is time consuming and therefore expensive and inconvenient for the patients who might still be immobilized for the purposes of medical imaging, or anesthetized. Moreover, final histopathologic analysis does not verify that the correct position on imagery has been sampled, but rather if the pathology matches the phenomenon presented in imagery. Measurement of the sample for the presence or a particular concentration of contrast agent using a method as described in this patent improves the accuracy of the intended sampling or surgical procedure.

FIG. 1 illustrates, by a way of a non-limiting example, a flow chart of a typical diagnostic and biopsy process as implemented currently. As the patient is prepared 101 to enter a biopsy procedure room, some preliminary imaging, test or analysis can be performed 102. Following this a contrast agent 103, specific to the imaging modality used, may be delivered into the patient via some method. The patient is then imaged with an imaging modality 104, to obtain an image regarding structures of clinical interest within the patient. An area of clinical significance 105 is then localized by a physician and a biopsy site 106 is targeted. Typically, the patient is then re-imaged to verify whether the biopsy site was selected appropriately 107. If a biopsy target site is not located in the clinically significant area (decision 108), the patient is re-imaged 104, or if correct site is selected, biopsy 108 of the suspicious region is then performed. The biopsy area is then re-imaged 110, to verify 111, whether the area of interest has been removed. If the clinically significant area is still present, the biopsy procedure is repeated starting with patient imaging 104. If the significant area is not visible with the imaging modality (111 Yes), the patient is then released 112. The biopsy sample is sent for further analysis to histopathology 121, where the sample is processed 122, and a determination is made whether the diagnosis is concordant with clinical expectations 123. A concordant diagnosis 123 ends with a final diagnosis of the patient 124. Non-concordant diagnosis requires a complete restart of the biopsy procedure 101, or patient management, or treatment through another means which is often more invasive.

The biopsy 109 is performed surgically or by utilizing specialized, minimally invasive biopsy tools. Of particular interest are large tissue sampling devices common to radiological practice for example the vacuum-assisted biopsy device presented by Hibner er al. (U.S. Pat Application No. 20030199753). The interface between the concentration measurement or detection device and the tissue sample may occur within tissue, be placed within the biopsy or surgical instrument, or in a separate specially designed container.

Often, it is difficult to determine whether the obtained sample corresponds precisely to the position within the body where the clinically significant lesion was found with an imaging modality. Typically, to verify that a biopsy was obtained from the appropriate site, the physician is guided by either applying similar imaging apparatus as that used for body imaging or with histopathology tests. Thus, verification of biopsy localization is often performed throughout the procedure at steps 108, 111 and 123. The process has to be repeated until a lesion containing sample is extracted or completed with non-conclusive or false diagnosis. Regardless of the results, this approach is very costly, and if diagnosis is wrong may lead to costly medical expenses through alternative procedures or legal process.

Figure 2:
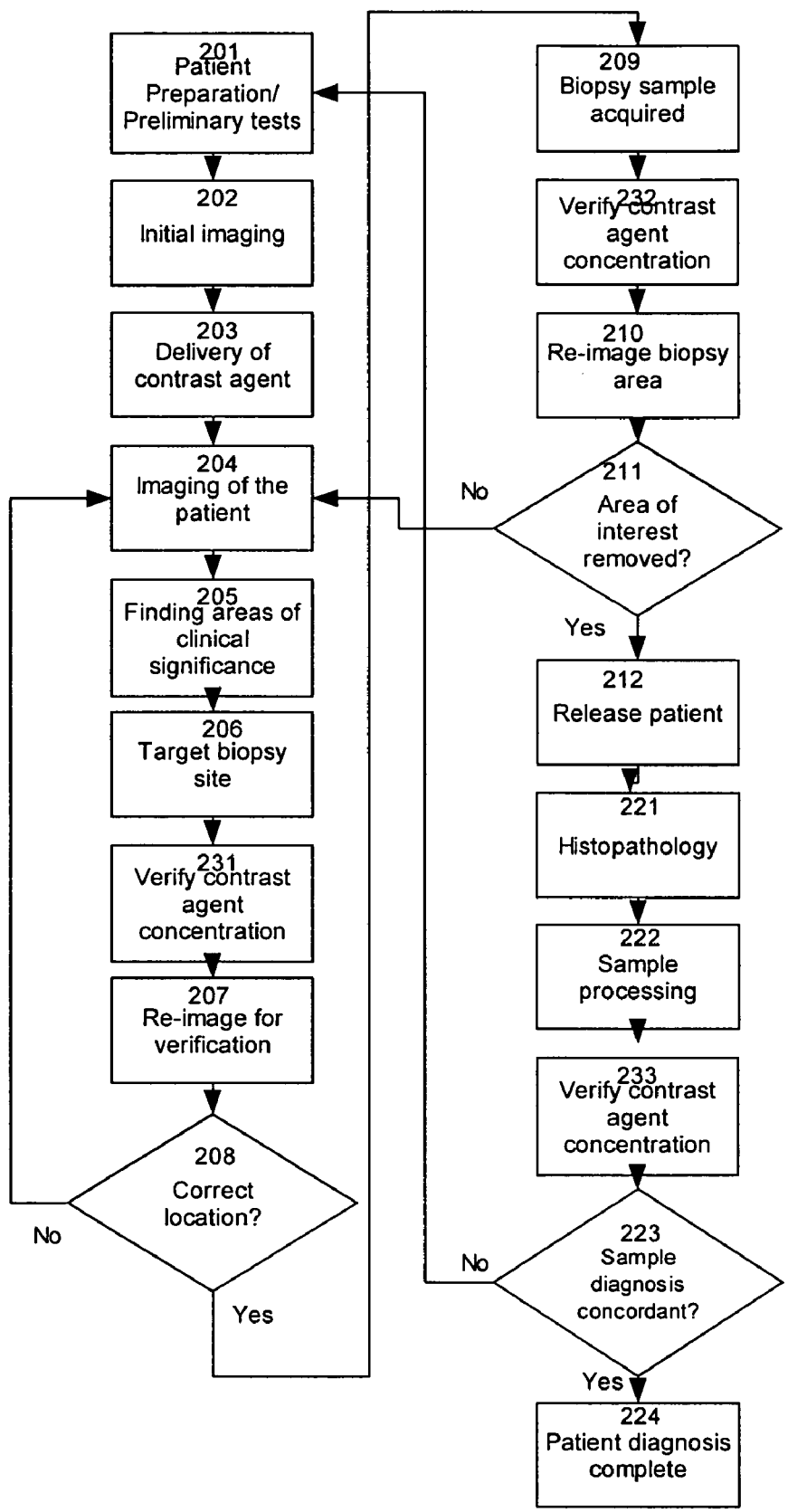
FIG. 2: Is a flowchart demonstrating the decision making process during a biopsy procedure, and where the presently described technology may contribute.

FIG. 2 illustrates, by a way of a non-limiting example, one embodiment of the described technology as it can be used in a typical biopsy procedure to independently verify whether a biopsy sample was taken from a clinically significant area as seen with an imaging modality, and which also accelerates the process of biopsy verification and reduces the risk of misdiagnosis.

Figure 3:
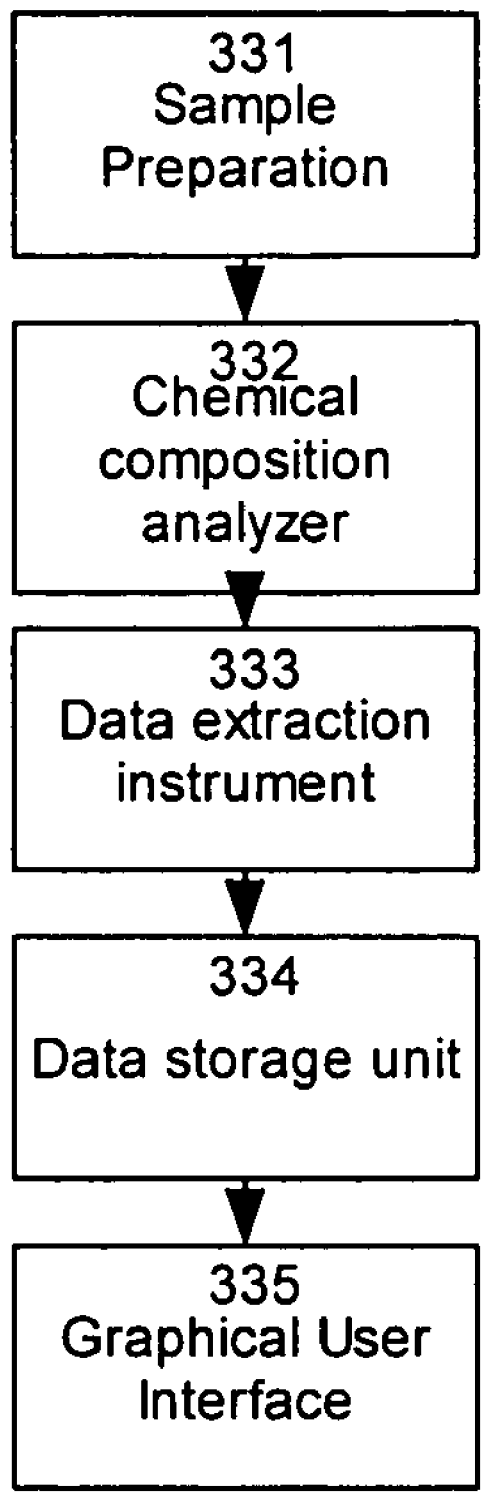
FIG. 3: Is a schematic block diagram generally presenting application of the invention for verification if biopsy sample contains abnormal concentration of the contrast agent.

FIG. 2 illustrates, by a way of a non-limiting example, one embodiment of the technology described herein as it can be used in a typical biopsy procedure. The initial steps 201 to 206 are the same with steps 101 to 106 of the presently applied process as illustrated in FIG. 1, with the exception that in step 202 some samples not affected by contrasting agent may be collected for reference purposes. Once, however, the biopsy site is targeted 206, it should be possible to insert a probe or otherwise determine the concentration or the presence of the imaging contrast agent 231. The concentration determination 231 can be done as shown in greater detail by FIG. 3. If elevated concentration of the imaging contrast agent is present at this point, the confidence of proper targeting of the biopsy site can be increased. This may or may not be used in parallel with imaging verification of needle or probe position. The detection of the contrast agent through a method as described in this patent has not been described in the Prior Art where emphasis has been on attempting in vivo diagnosis of the tissue area as demonstrated by Shafer-Peltier, et al, ("Raman microspectroscopic model of human breast tissue: implications for breast cancer diagnosis in vivo". *Journal of Raman Spectroscopy,* 2002), Nicole Kline et al ("Raman Chemical Imaging of Breast Tissue" *Journal of Raman Spectroscopy,* vol 28. 119-124 (1997)), and Webb et al (U.S. Pat App. US20031019397A1). Attempts to differentiate between healthy and diseased tissue in vivo are plagued with difficulties previous described. The overlooked application of using spectroscopy to assist in verification of the accuracy of the biopsy or surgical procedure has been neglected.

The biopsy sample extraction 209 follows, and another contrast agent concentration verification can be performed within the procedure room 232. The presence of significant amount of contrast agent within the biopsy sample can increase the confidence that the extracted sample is in fact from the area which presented as clinically significant during the imaging of the patient 204. The biopsy site may then be re-imaged either with or without the excised sample placed within the same imaging volume, to further increase the confidence of proper biopsy sample extraction. The benefits of re-imaging the sample include utilizing similar conditions to test for the presence of contrast agent within the tissue of interest both before and after a biopsy, thus increasing the confidence that if excised tissue appears to be similarly enhanced post biopsy, it does in fact contain the contrast agent responsible for the original image enhancement. This has not been addressed in any manner in the Prior Art. However, limitations to this implementation with respect to logistics of the procedure may be prohibitive. The biopsy procedure can then be followed as it is typically performed now, 110-122 and 210-222.

However, in the Histopathology lab, the presence of the imaging contrast agent may be verified once again to ensure that the sample has been obtained from an area which presented itself as clinically significant when imaged with the presence of contrast agent 233. Any combination of verification steps 231, 232 and 233 can be performed to increase the confidence that the sample has been extracted from the clinically significant area. Information obtained regarding the contrast agent concentration measurement can be utilized to better validate the histopathological diagnosis and imaging results.

The verification tests can be performed by applying some kind of apparatus for chemical composition analysis, whose role is to recognize whether the sample contains increased concentration of the contrast agent. The apparatus can include but not be limited to, an internally inserted probe equipped with light delivery and gathering ability, a non-contact imaging technique, or by an apparatus which can examine excised samples ex-vivo. In accordance with the present described technology and the inventions included therein, the biopsy sample 209 is prepared for a measurement of the contrast agent concentration with the use of many possible techniques, including but not limited to spectroscopy as described in the preferred embodiment of inventions described herein. Depending on the technique used in biopsy sample procurement, the sample might consist of tissue and fluids, fluids only or tissue with minimal fluid presence. The sample is then transferred or connected with the use of some device such as a fiberoptic probe, to a contrast agent measurement device presented in FIG. 3, for analysis of contrast agent concentration and data presentation. Optimally this is done while the patient is still immobilized in the device for the biopsy procedure, or undergoing surgery so as to affect the decision to remove more tissue. The first step 331 of this analysis is a sample preparation for the analysis and its transfer to within chemical composition analyzer 332. Any method and apparatus able to distinguish between low and high concentration of the contrast agent in the sample can be used for this purpose. This may include but is not limited to any method of chemical composition analysis known for these skilled in the art such as: analytical chemistry, colorimetry, classic spectroscopy in any spectral range (e.g., visible range, ultraviolet range, near infrared range, infrared range, etc.), using continuous and/or discrete set of wavelengths, produced by laser or non-laser radiation sources, spectroscopy of the scattered radiation in any known scattering mode (forward, backward, sideward or integrated by means of integrating cavity or sphere) using radiation as above, frustrated total internal reflection spectroscopy, Raman spectroscopy in any known mode, fluorescent spectroscopy with any kind of excitation, emission spectroscopy, Fourier Transform spectroscopy, absorption spectroscopy, spectral distribution of radiation in emission spectrum, flame spectroscopy, laser excited emission spectroscopy, mass spectroscopy, Auger spectroscopy, sonography, magnetic resonance spectroscopy or magnetic resonance imaging of the excised sample either separately or with the original imaging volume, where the collected signal provides information regarding a specific substance, and any other similar method. Optimally, the measurement procedure will not destroy or affect the sample, as further histopathological analysis would be required.

Very often such instruments are connected to some kind of data extraction instrument 303 and stored in data storage unit 334 from which data is taken for analysis with a digital data processing unit 310 in order to determine the concentration of the contrast agent of interest 231, 232, 233, and presented to physician by means of interface for example a Graphical User Interface (GUI) 335 in a form allowing for recognition of the concentration level of the contrasting agent in the sample. Based on the provided information, a decision is made, whether the sample under analysis has been obtained from the region of interest as detected by the imaging modality. If the sample is deemed not to come from the area of interest, the biopsy procedure is repeated immediately, while the patient is still present in the procedure room. The process is repeated until the sample with contrasting agent concentration indicates high probability that the sample has been collected from the proper place and is concordant with imagery appearance. This allows for savings of time, extra imaging and unnecessary delays in biopsy sample acquisition. This approach provides independent verification that sample has been collected from the proper place, reducing in this way the probability of misdiagnosis and, if proper analysis method is used, may greatly accelerate the whole diagnostic process reducing its cost and patient suffering.

Thus, if there existed an efficient method to detect the concentration of these contrast agents in a tissue sample, it would be possible to tell whether the excised tissue under examination is from a region with high contrast agent concentration; therefore, is of clinical interest, or is from the area with low concentration of the contrast agent, thereby from an area of low clinical interest.

Many of the methods mentioned previously, require either lengthy sample preparation process or cause sample destruction. Since the sample has to be further tested in histopathology laboratory, the methods which do not damage, modify or destroy the samples, or do so in a minimally-destructive way such that histopathologic analysis is minimally affected, and which can simultaneously recognize contrasting agents used for different imaging modalities are the most preferred. Fortunately, all substances used as contrast agents for different modalities contain the chemical components which are normally not present, or present in trace amounts within the body; therefore, their response to the electromagnetic radiation differs from that caused by molecules typically present in biological tissues, including water which has the highest concentration and produces extremely strong spectral response, especially in UV and in certain IR spectral ranges. The difference in the spectral response of the substances used as non-optical markers should allow for rapid measurement of their concentration with spectroscopic methods. There also exists the possibility of the use of an additional agent, combined with the contrast agent used for imaging purposes, to enhance the spectroscopic detectability of the imaging contrast agent in the region of clinical interest. This spectroscopic contrast agent may be bound to the imaging contrast agent, or administered separately.

In preferred embodiments, the contrast agent measurement device obtains spectroscopic information from the sample non-destructively, using one or more of the following functions or phenomena: colorimetry, classic spectroscopy in any spectral range, using continuous and/or discrete set of wavelengths, produced by laser or non-laser radiation sources, spectroscopy of the scattered radiation in any known scattering mode (forward, backward, sideward or integrated by means of integrating cavity or sphere) using radiation as above, frustrated total internal reflection spectroscopy, Raman spectroscopy in any known mode, fluorescent spectroscopy with any kind of excitation, emission spectroscopy, Fourier Transform spectroscopy, absorption spectroscopy, spectral distribution of radiation in emission spectrum, flame spectroscopy, laser excited emission spectroscopy, mass spectroscopy, Auger spectroscopy, sonography, magnetic resonance spectroscopy or magnetic resonance imaging of the excised sample either separately or with the original imaging volume, where the collected signal provides information regarding a specific substance, and any other similar or non-destructively equivalent method. The block diagram of such system based on scattered light attenuation spectroscopy in most general form by a way of example, but not by way of limitation is shown in FIG. 4.

Figure 4:
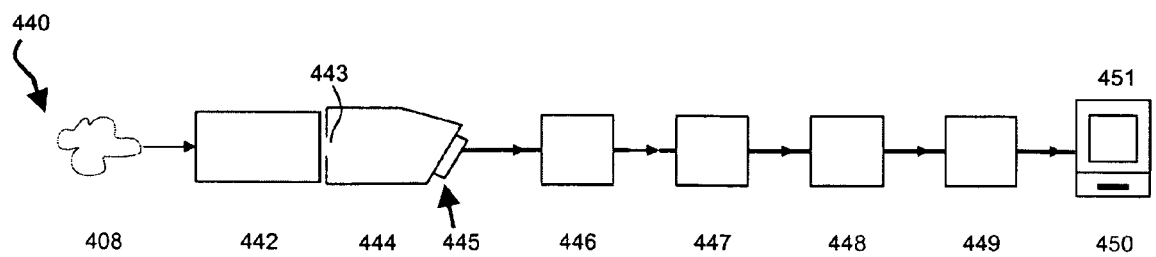
FIG. 4: Is a schematic block diagram presenting the preferred embodiment of the presently described technology including sample interface, spectrum analyzer and readout mechanisms.

FIG. 4 illustrates the structure of such an instrument, which in one embodiment may be, by way of non-limiting example, based on an optical high performance spectrometer. Broad band electromagnetic radiation 440, possibly transformed by a suitable optical system (not shown on the drawing), interacts with the excised biopsy sample 408, placed in an interface (also not shown on drawing) to be then collected by radiation collecting and delivery optics 442. The captured radiation is delivered to an entry port 443 of a spectrum disperser 444. Spectrum disperser 444 performs spatial separation of radiation into different wavelengths for each point of the entry port and delivers it to the photo detector array 445, which transforms a photometric signal into an electrical signal. The electrical signal is captured by an electronic circuit 446 and is converted to a digital form with an analog/digital converter 447. The digital signal is then pre-processed by digital signal processing unit 448, and information is stored in memory 449. The information can be accessed by one or more external computers 450 for further analysis, and presented to users through a graphic user interface 451. As a result, the determination if the sample has been taken from the proper area can be reached much faster and with higher certainty; therefore, accelerating whole testing process, reducing its cost, providing independent verification and increasing the probability that the excised sample had been collected appropriately.

It is understandable to all these skilled in the art, that many variations of the above instrument including these with different ways to produce radiation to form illumination beam to illuminate and hold sample, to collect radiation from the sample, to form beam for analysis, to perform analysis, collect, store and process data and finally to present data for the user can be used without departure from the proposed technology and inventions described herein.

Figure 5:
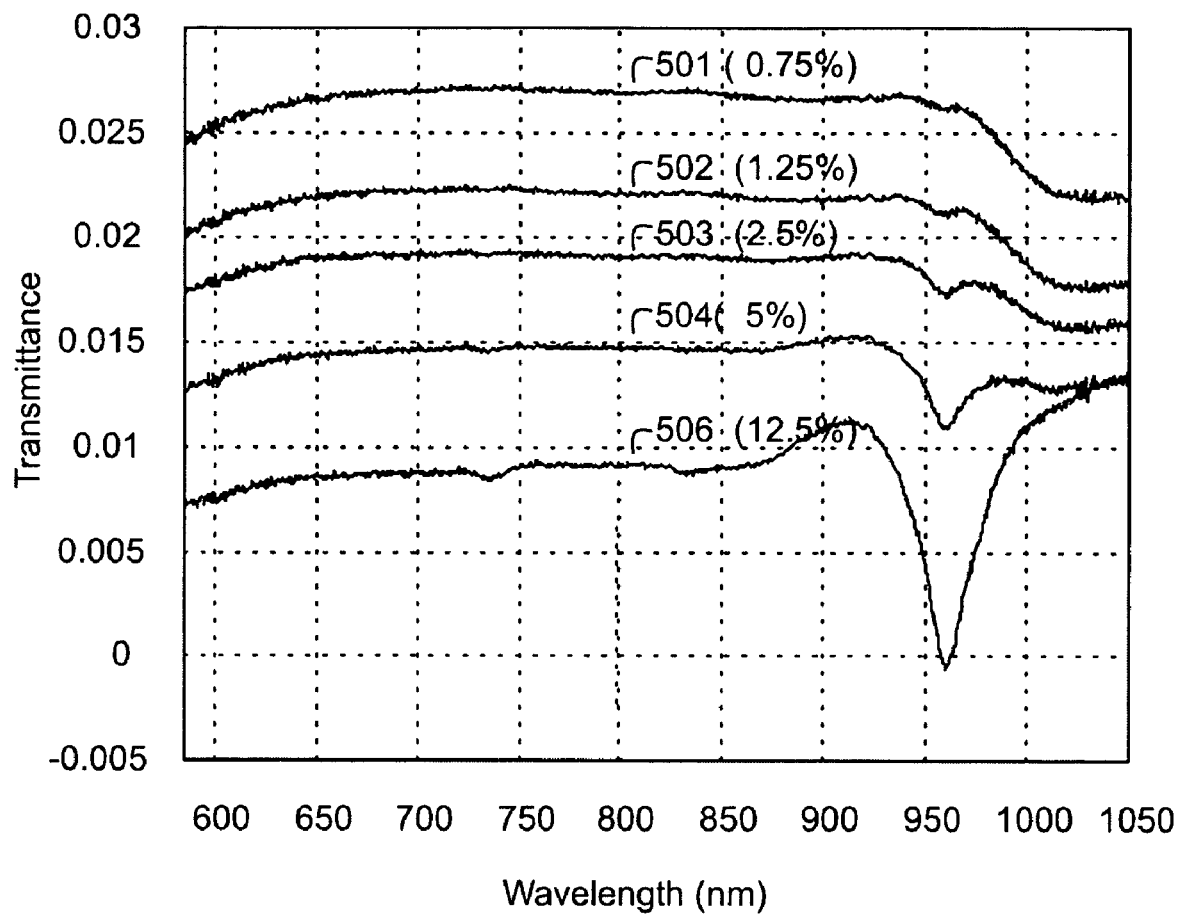
FIG. 5: Presents a graphic example of spectral changes due to the presence of a contrast agent in water solution. Water replacement has been corrected so that only concentration of the contrast agent is affecting the spectrum.

FIG. 5 illustrates, as a way of example but not by way of limitation, a spectroscopic comparison of five water solutions of various concentration of a typical contrast agent used in magnetic resonance imaging for the purpose of locating cancerous lesions. This illustrates one possible embodiment of the method used to determine concentration and shows that spectroscopic method does differentiate between solutions with different concentrations of contrasting agents. To our knowledge, this has not been accomplished in any comparable form in the Prior Art. The curves 501-505 represent calibrated and normalized transmittance data obtained with a high performance optical spectrometer in the 580 to 1050 nm range. The curves 501, 502, 503, 504, 505 represent by-volume concentrations of 0.75%, 1.25%, 2.5%, 5% and 12.5% of the contrast agent in pure water. As can be observed, there is a significant difference between the curves obtained for the various concentrations.

Figure 6:
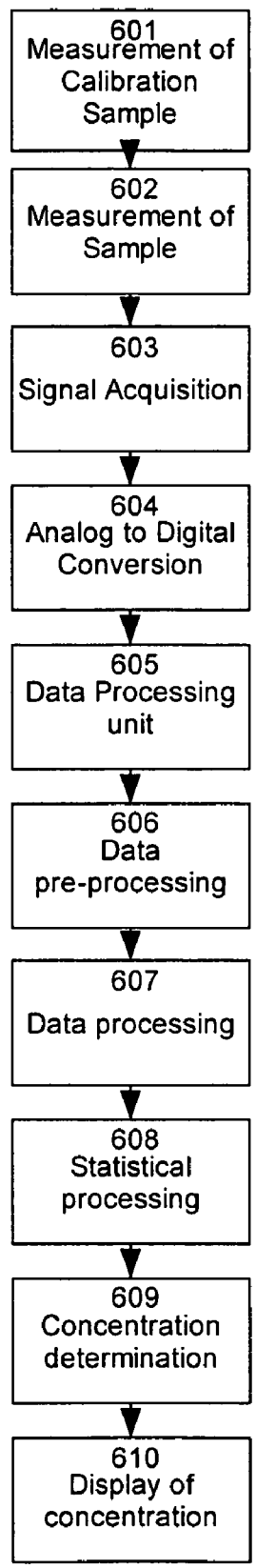
FIG. 6: Presents a flowchart of an example of a procedure for analysis of spectral data for the purpose of concentration determination, as proposed in one alternative embodiment of the presently described technology.

FIG. 6 shows a block diagram illustrating generally one embodiment of the process of measuring and displaying the contrast agent concentration. As a way of example but not by way of limitation, the use of a high performance absorbance spectrometer is proposed to obtain signals from the samples. This can be also performed using any other method of determining concentration of a contrast agent in the obtained sample.

In one embodiment of the described technology that is within the scope of inventions disclosed herein, a calibration sample 601 is measured prior to the sample measurement 602 to identify possible natural trace concentrations of the contrast agent in the normal tissue or to be used as a comparison with eventually obtained sample containing the contrast agent. In both cases the extracted samples are prepared for measurement in a way which is appropriate to the type of the sample and the type of contrast agent used. The samples are then characterized with a measurement device, in the preferred embodiment, a high performance scattered radiation spectrometer working in a spectral range most suitable for the contrast agent of interest. The signal produced by the instrument is acquired 603, digitized 604 and stored in computer memory 605. It is then processed with a data processing unit 606, where data is tested for consistency and preprocessed. The data pre-processing 607 may include one or more but is not limited to: dark signal subtraction, signal normalization for integration time, signal averaging, filtration, noise reduction, signal enhancement, signal smoothing, using linear approximation, quadratic and any higher order polynomial approximation, spline approximation, differentiation, integration, first or higher order derivative calculation, or averaging over any number of points or measurements, subtraction of unnecessary information, signal segmentation, signal differentiation, signal integration, or other manipulation of data to improve the qualities of the signal to be analyzed. Other corrections, based on imaging technique, tissue composition and the contrast agent may be implemented. These corrections are dependent on the biological process under investigation, the type of contrast agent, type of biopsy sample or surgical procedure, the time elapsed between imaging to sampling and sampling to spectrometer measurement as well as environmental conditions. Further calibration of the measurements may further be enhanced by additional information related to; unique properties of the exogenous agent, known database of a combination of exogenous marker and endogenous signals, patient or pathology specific data acquired a priori to sample measurement, patient or pathology specific reference measurements obtained in vivo and other factors having impact on the collected signal. The analysis of the stored data may be performed by direct visual observation of displayed data, displayed images, or virtual displays of graphic or graphically enhances data. The analysis may be automatically performed by software and/or algorithms that evaluate the raw or enhanced data based on predetermined standards of concentration, density, intensity, color, refraction, reflection, sonic variation, hue and other characteristics that are provided by the analysis. Combinations of the direct visual and automated system may also be used, wherein data is collected, software and/or algorithms enhance the data or translate it into a different format (by way of non-limiting examples, electrical resistance data is converted to color variations, bathochromic shifts are enhanced to magnify observable differences, only specific color variations or degrees of color variations are shown in two distinct colors, etc.), and an observer views displayed data in graphic, symbolic or alphanumeric form. An exemplary software format could evaluate absolute optical densities in an image, relative optical densities, absolute color densities, relative color densities, absolute or relative granularity, edge features between image segments, and any other image property that can be use to define differences in tissues that might be indicative of normal versus abnormal tissue images. It is likely that automated analysis would be backed up or supplemented by visual analysis. Further user-interface cues such as auditory signals or vibro-tactical indications may be used in concert with, or independent of such visual signals. Mechanically readable cues of any functional source may be used in this manner Once the signal pre-processing is completed, statistical methods 608 routinely applied for spectral composition analysis often referred to as chemometry are applied for spectral analysis. These methods can include one or more, but are not limited to partial least square regression, principal component analysis, neural networks, wavelet transforms, clustering and any modification of the above methods as well as any other method known for these skilled in the art, alone or in combination, possibly enhanced by other techniques such as genetic algorithms, Monte Carlo methods, mathematical simulation of noise or errors, wavelength standardization using any approximation method, photometric signal correction for offset, dark noise contribution, response non-linearity, smoothing, averaging, derivative calculation, integration, or other similar techniques, and any other signal processing methods whose aim is to extract information from the spectral signal. The spectral information is then used to find the concentration 609 of the specific contrast agent. The concentration of the contrast agent is then presented on a display 610, demonstrated or transferred by any method to the final decision maker (person, computer or a computer network) for the determination whether the sample was obtained from a clinically significant location, which was seen as an enhanced area using the contrast agent enhanced image. This information is then used to make a decision regarding further patient management: whether at least another biopsy should be performed to extract a more suitably localized sample or whether to accept the already extracted sample for pathological test and patient release. Since the spectroscopic measurement and subsequent decisions can be performed within a short time period, the patient can still remain in the imaging apparatus until the clinician has confidently sampled the region of interest. Similarly, in minimally invasive or surgical procedures, this information may be used to guide the resection of clinically significant tissue to ensure partial or complete resection.

The terminology of "non-destructive or minimally non-destructive" testing (referred to in this text as "NDT") has been used throughout this text. The terminology has a number of implications and can be used in at least two restrictive interpretations. It is desirable or even necessary that after the NDT, a more quantitative and formal analysis of the tissue must be or may be performed by traditional technician observation of cell tissue. To enable what may be legally or jurisdictionally required or preferred medical practice, there must be tissue available for this subsequent evaluation. To preserve tissue, all or a significant portion of the tissue (in a subsequently analyzable form) must remain intact. In such formats as described above, the NDT may consist of observation of the tissue my methods that may merely observe the contrast material, excite the contrast material for observation, or otherwise require only observational techniques. This would tend to involve a high level or complete preservation or non-destruction of the entire tissue sample. Other techniques might involve removal of liquid material only (e.g., blood, serum, ambient fluid, etc.) from the tissue sample to capture dissolved contrast or signature materials that would have been locally concentrated in the tissue because of the abnormality. For example, even radioactive materials with a propensity for absorption by abnormal tissues might be used, and a level of radioactivity might be measured to determine concentrations in sample. This removed liquid could thus be tested, and even though the mass of the sample and some minor mass of tissue might be removed, the tissue would be sufficiently intact for any subsequent quantitative testing or analytical testing. This tissue sample (with liquid withdrawn) is representative of an NDT that borders on pure tissue non-destructive testing and might be called minimally destructive by some personnel. Still other techniques might require that a small percentage of the remove sample (e.g., less than 25%, less than 20%, less than 15%, less than 10%, less than 8%, less than 5%, less than 3%, and even less than 2%) of the removed sample actually be decomposed for appropriate analysis, preserving the remaining tissue for subsequent and more thorough quantitative analysis. Although this technique actually destroys a portion of the tissue, it may be considered minimally non-destructive testing as a significant and preferably vast majority of the removed tissue sample is preserved in a complete form that can be analyzed by the most exacting (e.g., visual field observation) standard techniques for tissue analysis.

The techniques described herein may be used on any animal samples, including both human and non-human tissue samples. The contrast materials or other exogenous materials may be provided to the patient by any convenient and effective manner (as is known for the individual materials). For example, some materials may be orally ingested, others may be intravenously introduced, others may be injected by syringe, including either intravenously, mass tissue injection or subcutaneously. Certain materials my be applied transdermally, especially where suspected abnormal tissue areas are near the surface of the skin (e.g., dermal tissue, surface tumors, and the like).

The above description has provided numerous specific embodiments and examples within the scope of the technology that includes inventions to be claimed herein. This content of the description is not intended to be limiting on the scope of inventions that can and are claimed herein. The examples are merely species within the genus of technology that has been contemplated herein.

We claim:

1. A method for indicating a likely presence of abnormal tissue within an ex vivo biopsy sample of tissue of a living patient comprising:

providing observable agent to an in vivo region of surgical interest of the living patient;

removing from the living patient a biopsy tissue sample from the region of interest to provide a removed tissue sample;

minimally-destructively observing the removed tissue samples under conditions that allow observation or detection of the observable agent; and evaluating results of the observation or detection of the observable agent within the removed tissue sample while the patient is still living to confirm that tissue was removed from the region of surgical interest of a still living patient that had been provided with the observable agent in vivo.

2. The method of claim 1 wherein evaluating results comprises assessing a likelihood of the presence of abnormal tissue in the still living patient within a sample and non-destructively observing the removed tissue.

3. The method of claim 1 wherein evaluating results comprises assessing whether the removed tissue sample has been taken from the region of interest in a still living patient and non-destructively observing the removed tissue.

4. The method of claim 1 wherein non-destructively observing is performed by a step comprising spectroscopic analysis while the patient is still living.

5. The method of claim 1 wherein after evaluating results, histopathic examination is performed on the removed tissue sample while the patient is still living.

6. The method of claim 1 wherein non-destructive observation is used and observing comprises at least one procedure selected from the group consisting of colorimetry, sonography, spectroscopy, and magnetic resonance imaging of the removed tissue sample.

7. The method of claim 6 wherein the spectroscopy is selected from the group consisting of scattered radiation spectroscopy, frustrated total internal reflection spectroscopy, Raman spectroscopy, fluorescent spectroscopy, emission spectroscopy, Fourier transform spectroscopy, flame spectroscopy, laser excited emission spectroscopy, mass spectroscopy, Auger spectroscopy, magnetic resonance spectroscopy.

8. The method of claim 6 where intensity changes or density differences from the removed tissue sample provide information that is evaluated.

9. The method of claim 1 wherein the observable agent is known to be absorbed differently by normal tissue and abnormal tissue.

10. The method of claim 1 wherein non-destructive observation is used and the non-destructive observation comprises assessing concentration of the observable agent in the tissue by measuring or detection of absorption of electromagnetic radiation at least one preselected wavelength or one or more spectral bands in at least one of the UV, visible and IR spectral ranges without the damage to the tested tissue.

11. The method of claim 1 wherein a non-destructive observation is used and the non-destructive observation comprises concentration measuring techniques.

12. The method of claim 1 wherein evaluating results includes treatment of obtained measurement or observation data by at least one data approximation technique selected from the group consisting of linear approximation, quadratic and any higher order approximation, polynomial approximation and spline approximation.

13. The method of claim 1 wherein the evaluating of results comprises approximating concentration of the observable agent in the removed tissue sample.

14. The method of claim 13 wherein approximating concentration comprises a step of absorption spectroscopy in at least one of the ultraviolet, visible and infrared spectral ranges.

15. The method of claim 14 wherein the absorption spectroscopy comprises concentration measurement of the observable agent in the removed tissue sample applying spectroscopy at selected wavelengths of one or more continuous spectral bands of radiation scattered by the removed tissue sample.

16. The method of claim 1 wherein evaluating results includes treatment of obtained data by at least one signal processing technique selected from the group consisting of: instrument calibration, dark signal subtraction, signal normalization for integration time, signal averaging, filtration, noise reduction, signal enhancement, signal smoothing, using linear approximation, quadratic and any higher order polynomial approximation, spline approximation, differentiation, integration, first or higher order derivative calculation, averaging over any number of points or measurements, subtraction of unnecessary information, signal segmentation, or other manipulation of data to improve the qualities of the signal to be analyzed.

17. The method of claim 1 wherein evaluating results includes the analysis of obtained data by at least one signal analysis technique selected from the group consisting of: partial least square regression, principal component analysis, neural networks, wavelet transforms, clustering, genetic algorithms, Monte Carlo methods, mathematical simulation of noise or errors, signal standardization using any approximation method, photometric signal correction for offset, dark noise contribution, response non-linearity, smoothing, averaging, derivative calculation, integration, or other manipulation of data to improve the extraction of information from the observed signal.

18. A method for indicating a likely presence of abnormal tissue within an ex vivo sample of tissue comprising:

providing observable agent to a region of surgical interest of a live patient;

removing from the live patient a tissue sample from the region of surgical interest to provide a removed tissue sample;

or minimally-destructively observing the removed tissue samples under conditions that allow observation or detection of the agent by scattered radiation spectroscopy while the patient is alive; and evaluating results of the observation or detection of the observable agent within the removed tissue sample while the patient is alive to living to confirm that tissue was removed from the region of surgical interest of a still living patient.

19. The method of claim 18 wherein non-destructive observation is performed.

* * * * *